(12) United States Patent
Kim

(10) Patent No.: US 9,295,451 B2
(45) Date of Patent: Mar. 29, 2016

(54) ULTRASOUND SYSTEM FOR PROVIDING AN ULTRASOUND IMAGE OPTIMIZED FOR POSTURE OF A USER

(75) Inventor: Jung Soo Kim, Seoul (KR)

(73) Assignee: SAMSUNG MEDISON CO., LTD, Kangwon-Do (KR)

( * ) Notice: Subject to any disclaimer, the term of this patent is extended or adjusted under 35 U.S.C. 154(b) by 320 days.

(21) Appl. No.: 13/306,339

(22) Filed: Nov. 29, 2011

(65) Prior Publication Data

US 2012/0136254 A1    May 31, 2012

(30) Foreign Application Priority Data

Nov. 29, 2010    (KR) .................. 10-2010-0119282

(51) Int. Cl.
```
A61B 8/00      (2006.01)
G06F 1/16      (2006.01)
G01S 7/52      (2006.01)
G06F 3/01      (2006.01)
```

(52) U.S. Cl.
CPC ............. *A61B 8/462* (2013.01); *A61B 8/463* (2013.01); *G01S 7/52* (2013.01); *G06F 1/1601* (2013.01); *G06F 3/013* (2013.01); *G09G 2320/0261* (2013.01); *G09G 2340/045* (2013.01)

(58) Field of Classification Search
CPC ........ A61B 8/463; A61B 8/462; G06F 3/013; G06F 1/1601; G09G 2340/045; G09G 2340/0261; G01S 7/52
USPC ............. 600/443; 250/205, 208.1; 340/901; 378/117; 700/245
See application file for complete search history.

(56) References Cited

U.S. PATENT DOCUMENTS

| | | | |
|---|---|---|---|
| 7,851,736 B2* | 12/2010 | Spahn | 250/205 |
| 8,115,877 B2* | 2/2012 | Blatchley et al. | 348/836 |
| 2003/0234799 A1* | 12/2003 | Lee | 345/660 |
| 2004/0160386 A1* | 8/2004 | Michelitsch et al. | 345/10 |
| 2007/0276244 A1 | 11/2007 | Sui | |
| 2008/0049020 A1* | 2/2008 | Gusler et al. | 345/427 |

(Continued)

FOREIGN PATENT DOCUMENTS

| | | | |
|---|---|---|---|
| JP | 2000-066610 A | 3/2000 | |
| JP | 2006-167043 A | 6/2006 | |

(Continued)

OTHER PUBLICATIONS

European Search Report issued in European Patent Application No. 11190551.9 issued on Mar. 22, 2012.

*Primary Examiner* — Long V Le
*Assistant Examiner* — Helene Bor
(74) *Attorney, Agent, or Firm* — McDermott Will & Emery LLP

(57) ABSTRACT

Embodiments of an ultrasound system for detecting a posture of a user and providing an optimal ultrasound image for the posture of the user are disclosed. The ultrasound system includes a display unit including a sensing unit installed in one side of a monitor. The sensing unit detects a position of a user, a distance between the user and the monitor, a height of the user with respect to the monitor and a viewing angle of the user toward the monitor to thereby form and output sensing signals corresponding thereto. The ultrasound system further includes a processing unit coupled to the sensing unit. The processing unit forms the ultrasound image by using ultrasound data and performs optimal image processing for the posture of the user upon the ultrasound image based on the sensing signals.

8 Claims, 9 Drawing Sheets

(56) References Cited

U.S. PATENT DOCUMENTS

2009/0164896 A1* 6/2009 Thorn ............................ 715/700
2010/0007852 A1* 1/2010 Bietry et al. ...................... 353/8
2012/0229300 A1* 9/2012 Fu ................................ 340/901

FOREIGN PATENT DOCUMENTS

| KR | 2004-0023088 A | 3/2004 |
| KR | 10-2010-0052005 A | 5/2010 |

* cited by examiner

US 9,295,451 B2

ULTRASOUND SYSTEM FOR PROVIDING AN ULTRASOUND IMAGE OPTIMIZED FOR POSTURE OF A USER

CROSS-REFERENCE TO RELATED APPLICATION

This application is based upon and claims the benefit of priority from Korean Patent Application No. 10-2010-0119282 filed on Nov. 29, 2010, the entire disclosure of which is incorporated herein by reference.

TECHNICAL FIELD

The present invention generally relates to ultrasound systems, and more particularly to an ultrasound system for providing an ultrasound image optimized according to the posture of a user.

BACKGROUND

An ultrasound system with non-invasive and non-destructive nature has been extensively used in the medical field to obtain information on an inside of a target object. Such an ultrasound system provides a doctor in real time with a high resolution image of the inside of the target object without the need to perform any surgical operation, which can be used to play an important role in the medical field.

The ultrasound system transmits ultrasound signals to the target object, receives the ultrasound signals (i.e., ultrasound echo signals) reflected from the target object, and performs signal processing upon the received ultrasound echo signals to thereby acquire ultrasound data. The ultrasound system performs scan conversion or rendering processing upon the acquired ultrasound data to form an ultrasound image.

When using the ultrasound system, a user adjusts manually a position and/or an angle of a monitor in a three-dimensional direction (e.g., up/down and/or right/left) according to a position (i.e., posture) of the user. Such an ultrasound system is not user-friendly since the user adjusts manually the position and/or the angle of the monitor while acquiring the ultrasound images of the target object. Further, since the ultrasound system provides a fixed ultrasound image regardless of the posture of the user, the user must change his/her posture to see the ultrasound image displayed on the monitor.

SUMMARY

The present invention provides some embodiments of an ultrasound system for detecting the posture of a user and providing an optimal ultrasound image for the posture of the user.

According to one embodiment of the present disclosure, an ultrasound system comprises: an ultrasound data acquisition unit configured to transmit ultrasound signals to a target object and receive ultrasound echo signals reflected from the target object to thereby acquire ultrasound data; a display unit including a monitor configured to display an ultrasound image; a sensing unit installed in one side of the monitor and configured to detect a position of a user, a distance between the user and the monitor, a height of the user with respect to the monitor and a viewing angle of the user toward the monitor to thereby form and output sensing signals corresponding thereto; a storage unit configured to store optimal posture information for providing an optimal ultrasound image for the posture of the user; and a processing unit coupled to the ultrasound data acquisition unit, the sensing unit and the storage unit, the processing unit being configured to form the ultrasound image by using the ultrasound data and perform an optimal image processing for the posture of the user upon the ultrasound image based on the sensing signals and the optimal posture information.

According to another embodiment of the present disclosure, an ultrasound system comprises: an ultrasound data acquisition unit configured to transmit ultrasound signals to a target object and receive ultrasound echo signals reflected from the target object to thereby acquire ultrasound data; a display unit including a monitor configured to display an ultrasound image and a driving section configured to move the monitor in a three-dimensional direction; a sensing unit installed in one side of the monitor and configured to detect an attitude of the monitor, a position of a user, a distance between the user and the monitor, a height of the user with respect to the monitor and a viewing angle of the user toward the monitor to thereby form and output sensing signals corresponding thereto; a storage unit configured to store optimal posture information for providing an optimal ultrasound image for the posture of the user; and a processing unit coupled to the ultrasound data acquisition unit, the display unit, the sensing unit and the storage unit, the processing unit being configured to form the ultrasound image by using the ultrasound data and perform moving of the monitor by driving the driving section, or both moving of the monitor by the driving section and optimal image processing upon the ultrasound image, based on the sensing signals and the optimal posture information.

DETAILED DESCRIPTION

A first embodiment of the present disclosure will now be described in detail with reference to the drawings.

First Embodiment

Figure 1:
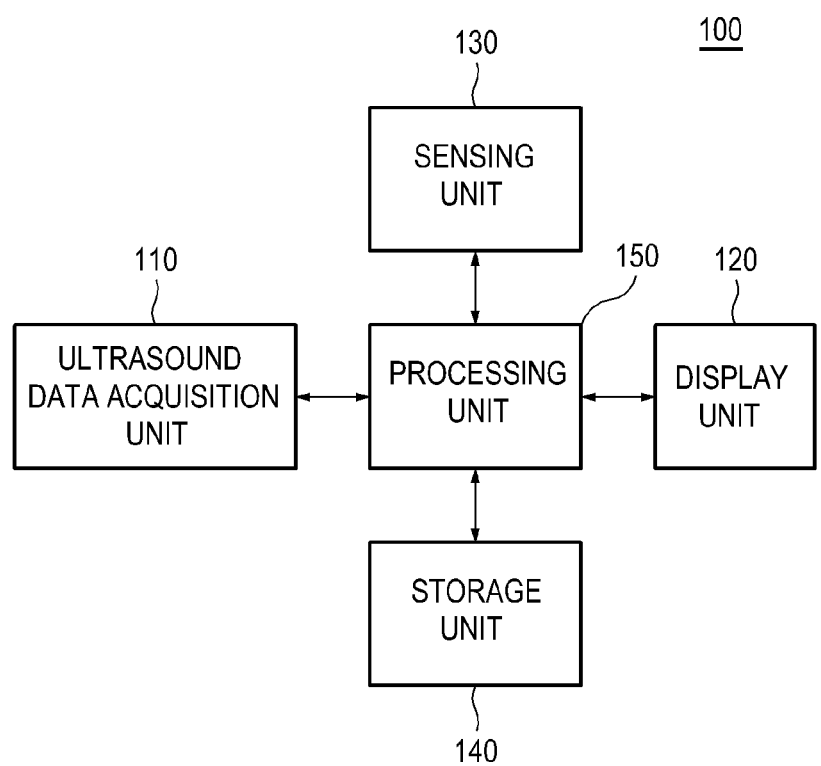
FIG. 1 is a block diagram showing an ultrasound system according to a first embodiment.

FIG. 1 is a block diagram showing an ultrasound system according to a first embodiment of the present disclosure. Referring to FIG. 1, an ultrasound system 100 may include an ultrasound data acquisition unit 110, a display unit 120, a sensing unit 130, a storage unit 140 and a processing unit 150.

The ultrasound data acquisition unit 110 may transmit ultrasound signals to a target object and receive the ultrasound signals (i.e., ultrasound echo signals) reflected from the target object to thereby acquire ultrasound data.

Figure 2:
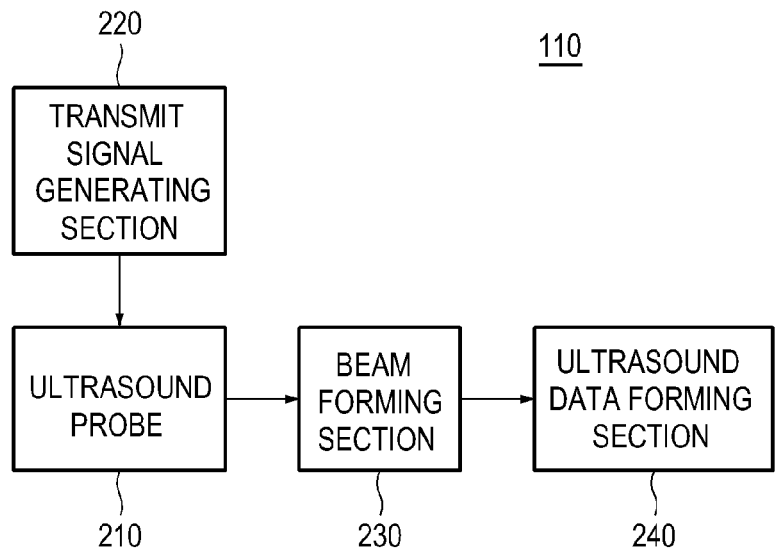
FIG. 2 is a block diagram showing an ultrasound data acquisition unit according to the first embodiment.

FIG. 2 is a block diagram showing the ultrasound data acquisition unit according to the first embodiment. Referring to FIG. 2, the ultrasound data acquisition unit 110 may include an ultrasound probe 210, a transmit signal generating section 220, a beam forming section 230 and an ultrasound data forming section 240.

The ultrasound probe 210 may include a plurality of transducer elements (not shown) configured to perform reciprocal conversion between electric signals and ultrasound signals. The ultrasound probe 210 may transmit the ultrasound signals to the target object along each of a plurality of scan lines (not shown) and receive the ultrasound echo signals reflected from the target object, thereby forming receive signals. The receive signal is an analog signal. The ultrasound probe 210 may be at least one of a convex probe, a linear probe and the like.

The transmit signal generating section 220 may be configured to control transmission of the ultrasound signals. The transmit signal generating section 220 may generate the transmit signals for acquiring an ultrasound image in consideration of the transducer elements and focal points. The ultrasound image may include a brightness mode (B-mode) image, a spectral Doppler image, a color Doppler image, a three-dimensional ultrasound image, an elasticity image and the like. The ultrasound probe 210 may convert the transmit signals provided from the transmit signal generating section 220 into the ultrasound signals and transmit the ultrasound signals to the target object. Further, the ultrasound probe 210 may receive the ultrasound echo signals reflected from the target object to thereby form the receive signals.

The beam forming section 230 may form digital signals by performing analog-to-digital conversion on the receive signals outputted from the ultrasound probe 210. The beam forming section 230 may further form receive-focused beams by receive-focusing the digital signals in consideration of the transducer elements and the focal points.

The ultrasound data forming section 240 may form the ultrasound data corresponding to the ultrasound image by using the receive-focused beams provided from the beam forming section 230. The ultrasound data may include radio frequency (RF) data or in-phase/quadrature (IQ) data, although the ultrasound data may not be limited thereto. Further, the ultrasound data forming section 240 may also perform a variety of signal processing (e.g., gain adjustment, etc.), which is necessary to form the ultrasound data, upon the receive-focused beams.

Referring back to FIG. 1, the display unit 120 may display the ultrasound image. In the present embodiment, the display unit 120 may include a monitor 121 (shown in FIGS. 3 and 4), the position and angle of which can be adjusted manually up and down and/or right and left, or a monitor fixed to the ultrasound system 100.

The sensing unit 130 may be installed on one side of the monitor 121. The sensing unit 130 may be configured to detect a position of the user, a distance between the user and the monitor 121, a height of the user with respect to the monitor 121 and a viewing angle of the user toward the monitor 121 to thereby form and output the sensing signals corresponding thereto.

Figure 3:
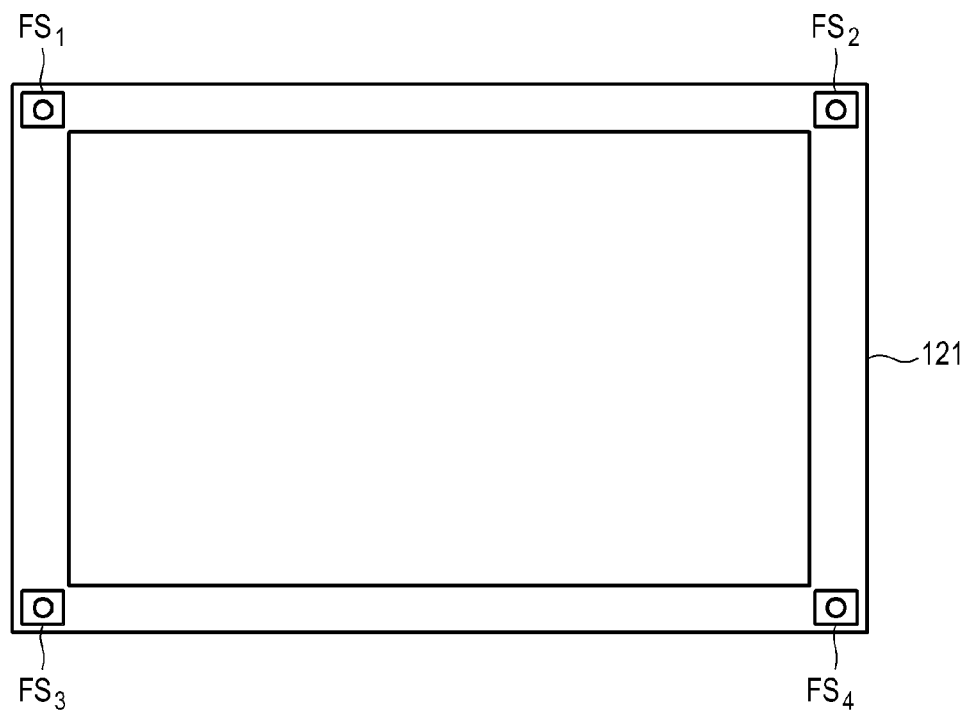
FIG. 3 is a schematic diagram showing an example of a sensing unit according to the first embodiment.

In one example, as shown in FIG. 3, the sensing unit 130, which is installed on one side (e.g., frame) of the monitor 121, may include first sensors $FS_1$ to $FS_4$ configured to detect the position of the user, the distance between the user and the monitor 121, the height of the user with respect to the monitor 121 and the viewing angle of the user toward the monitor 121 to thereby form and output the sensing signals corresponding thereto. Any device may be employed as the first sensors $FS_1$ to $FS_4$ as long as the device can detect the position of the user, the distance between the user and the monitor 121, the height of the user with respect to the monitor 121 and the viewing angle of the user toward the monitor 121, and form and output the sensing signals corresponding thereto. For example, the first sensors $FS_1$ to $FS_4$ may include at least one of a camera, a webcam and the like. The first sensors $FS_1$ to $FS_4$ may be provided inside or outside the monitor 121.

While the sensing unit 130 may include four first sensors $FS_1$ to $FS_4$ in the above-described example, one of ordinary skill in the art may fully understand that the number as well as the position of the first sensors can be varied as necessary, and not be limited to those described in the example.

Figure 4:
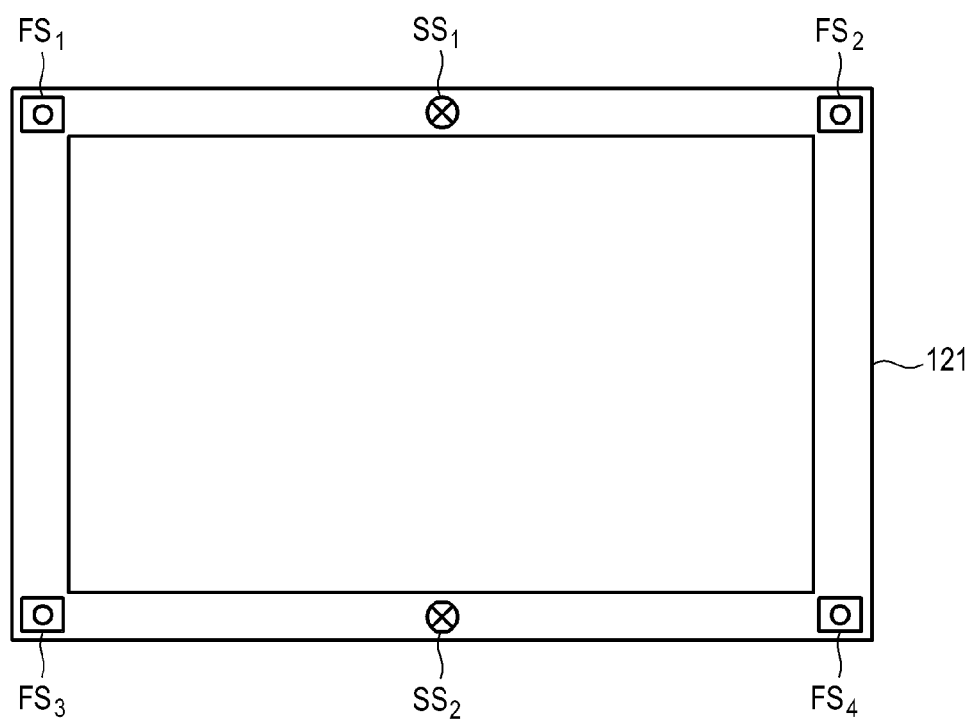
FIG. 4 is a schematic diagram showing another example of a sensing unit according to the first embodiment.

In another example, as shown in FIG. 4, the sensing unit 130, which is installed on one side (i.e., frame) of the monitor 121, may include first sensors ($FS_1$ to $FS_4$) configured to detect the position of the user, the height of the user with respect to the monitor 121 and the viewing angle of the user toward the monitor 121 to thereby form and output first sensing signals corresponding thereto. The sensing unit 130 may further include second sensors $SS_1$ and $SS_2$ configured to detect the distance between the user and the monitor 121 to form and output second sensing signals corresponding thereto. Any device may be employed as the second sensors $SS_1$ and $SS_2$ as long as the device can detect the distance between the user and the monitor 121, and form and output the sensing signals corresponding thereto. For example, the second sensors $SS_1$ and $SS_2$ may include a distance detecting sensor. The second sensors $SS_1$ and $SS_2$ may be provided inside or outside the monitor 121.

While the sensing unit 130 may include two second sensors $SS_1$ and $SS_2$ in the above-described example, one of ordinary skill in the art will fully understand that the number as well as the position of the second sensor can be varied as necessary, and not be limited to those described in this example.

The storage unit 140 may store optimal posture information necessary for providing optimal ultrasound image according to the posture of the user. In the present embodiment, the optimal posture information may include information on the optimal distance between the user and the monitor 121, the optimal height of the user with respect to the monitor 121 and the optimal viewing angle of the user toward the monitor 121.

The processing unit 150 may be coupled to the ultrasound data acquisition unit 110, the sensing unit 130 and the storage unit 140. The processing unit 150 may include at least one of a central processing unit (CPU), a microprocessor, a graphic processing unit (GPU) and the like.

Figure 5:
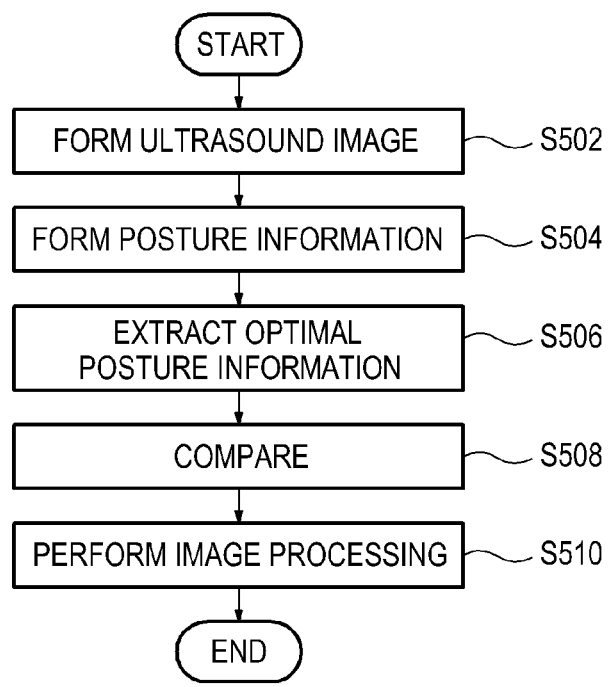
FIG. 5 is a flow chart showing a process of forming an optimal ultrasound image for posture of a user in accordance with the first embodiment.

FIG. 5 is a flow chart showing a process of forming the optimal ultrasound image for the posture of the user in accordance with the first embodiment. Referring to FIG. 5, the processing unit 150 may produce the ultrasound image by using the ultrasound data provided from the ultrasound data acquisition unit 110 at S502. The ultrasound image may be produced through scan conversion or rendering processing. The produced ultrasound image may be displayed on the monitor 121 of the display unit 120.

The processing unit 150 may be configured to form posture information, which indicates the posture of the user with respect to the monitor 121, based on the sensing signals provided from the sensing unit 130 at S504. In the present embodiment, the posture information may include the distance between the user and the monitor 121, the height of the user with respect to the monitor 121 and the viewing angle of the user toward the monitor 121. However, the posture information may not be limited thereto.

In one example, if the sensing signals are provided from the first sensors $FS_1$ to $FS_4$, then the processing unit 150 may be configured to detect the user's face (more preferably, the user's eyes) by using the provided sensing signals. The user's face can be detected through vision recognition (i.e., image recognition) and the like. By using the detected user's face as a reference point, the processing unit 150 may calculate the distance between the monitor 121 and the user, the height of the user with respect to the monitor 121 (i.e., height of the user's eyes with respect to the monitor 121) and the viewing angle of the user toward the monitor 121. Calculation of the distance, height and viewing angle can be performed by using a variety of well-known methods so that the detailed description thereof will be omitted in the present embodiment. In this way, the processing unit 150 may form the posture information including the calculated distance, height and viewing angle.

In another example, if the first sensing signals are provided from the first sensors $FS_1$ to $FS_4$, then the processing unit 150 may be configured to detect the user's face (more preferably, the user's eyes) by using the provided first sensing signals. The processing unit 150 may calculate the height of the user with respect to the monitor 121 (i.e., height of the user's eyes with respect to the monitor 121) and the viewing angle of the user toward the monitor 121 by utilizing the detected user's face as a reference point. Further, the processing unit 150 may be provided with the second sensing signals from the second sensors $SS_1$ and $SS_2$ and calculate the distance between the monitor 121 and the user by using the provided second sensing signals. In this way, the processing unit 150 may form the posture information including the calculated distance, height and viewing angle.

The processing unit 150 may be configured to extract the optimal posture information from the storage unit 140 at S506 and compare the extracted optimal posture information with the posture information to thereby acquire posture difference information at S508. The posture difference information may include respective differential values of the distance, height and viewing angle.

The processing unit 150 may be configured to perform image processing upon the ultrasound image based on the posture difference information and the posture information to obtain the optimal ultrasound image for the position of the user at S510. The ultrasound image with the optimal image processing performed may be displayed on the monitor 121 of the display unit 120.

In one example, if the ultrasound image is a two-dimensional or three-dimensional ultrasound image and the posture difference information includes the differential value of the distance, then the processing unit 150 may magnify or downscale the ultrasound image in proportion to the distance differential value included in the posture difference information. In another example, if the ultrasound image is a two-dimensional or three-dimensional ultrasound image and the posture difference information includes the differential value of the viewing angle, then the processing unit 150 may vertically or horizontally magnify/downscale the ultrasound image, or tilt or extend the ultrasound image toward the user, in proportion to the viewing angle differential value included in the posture difference information. In another example, if the ultrasound image is a three-dimensional ultrasound image and the posture difference information includes the differential value of the viewing angle, then the processing unit 150 may rotate the three-dimensional ultrasound image based on the viewing angle differential value included in the posture difference information.

Second Embodiment

Figure 6:
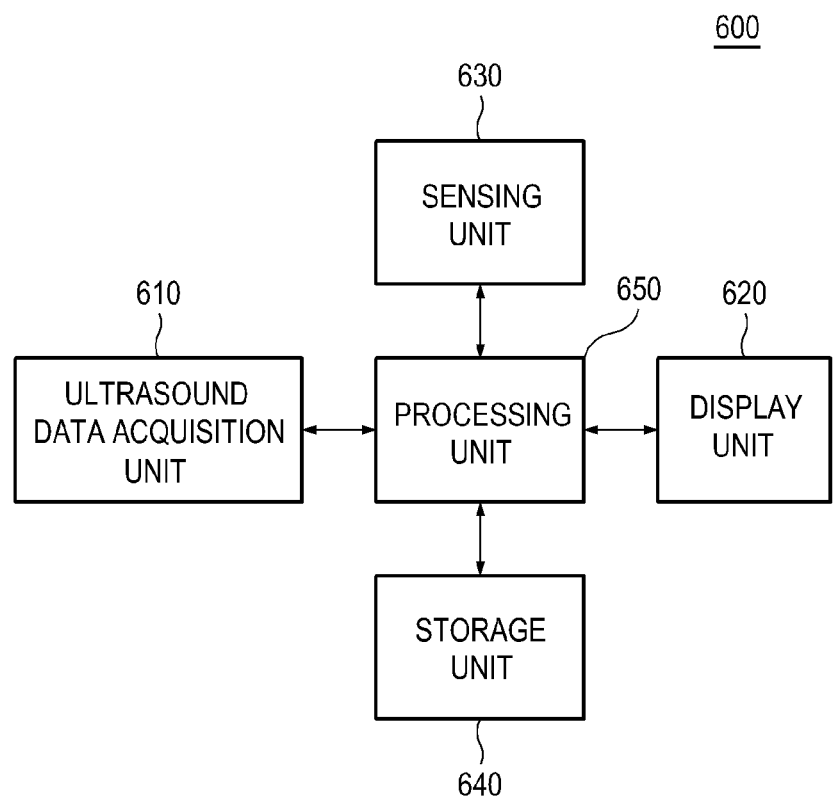
FIG. 6 is a block diagram showing an ultrasound system according to a second embodiment.

FIG. 6 is a block diagram showing a configuration of an ultrasound system in accordance with a second embodiment. Referring to FIG. 6, an ultrasound system 600 may include an ultrasound data acquisition unit 610, a display unit 620, a sensing unit 630, a storage unit 640 and a processing unit 650.

The ultrasound data acquisition unit 610 may be configured to transmit ultrasound signals to a target object and receive the ultrasound echo signals reflected from the target object to thereby acquire ultrasound data corresponding to an ultrasound image. The ultrasound data acquisition unit 610 in the present embodiment may be identically configured with the ultrasound data acquisition unit 110 in the first embodiment and thus will not be described in detail in this embodiment.

Figure 7:
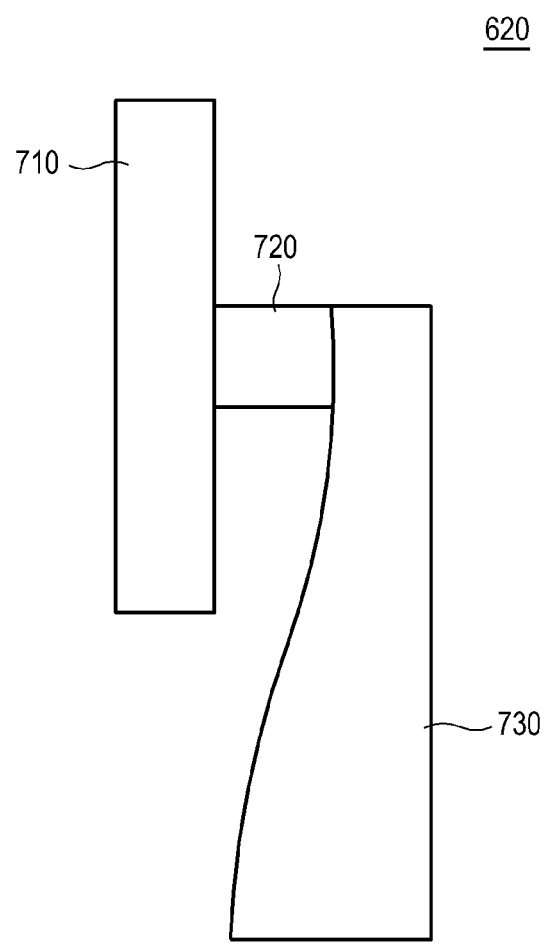
FIG. 7 is a schematic diagram showing an example of a display unit according to the second embodiment.

The display unit 620 may display the ultrasound image. In the present embodiment, the display unit 620 may include a monitor 710 configured to display the ultrasound image, a driving section 720 configured to move the monitor 710 in a three-dimensional direction (e.g., back/forth or right/left) and a supporting section 730 configured to support the driving section 720, as shown in FIG. 7. The driving section 720 may be embodied with the well-known devices so that the detailed description thereof will be omitted in the present embodiment.

The sensing unit 630 may be installed on one side of the monitor 710. The sensing unit 630 may be configured to detect a position of the user, a distance between the user and the monitor 710, a height of the user with respect to the monitor 710, a viewing angle of the user toward the monitor 710 and a three-dimensional position of the monitor 710 to thereby form and output sensing signals corresponding thereto.

Figure 8:
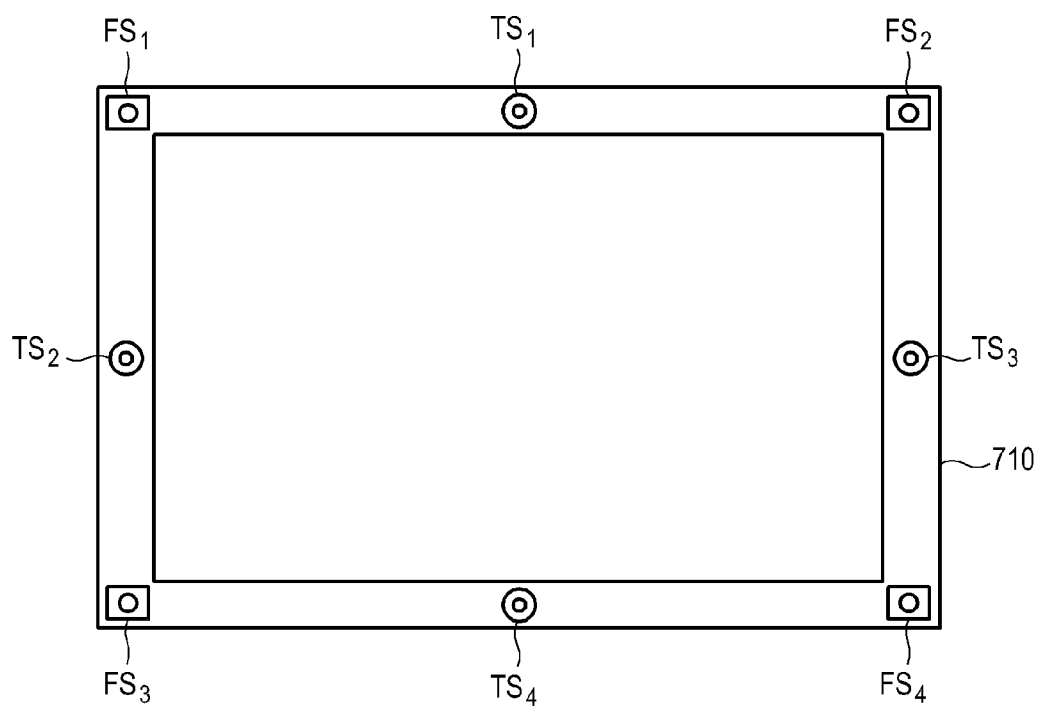
FIG. 8 is a schematic diagram showing an example of a sensing unit according to the second embodiment.

In one example, as shown in FIG. 8, the sensing unit 630, which is installed on one side (e.g., frame) of the monitor 710, may include first sensors $FS_1$ to $FS_4$ configured to detect the position of the user, the distance between the user and the monitor 710, the height of the user with respect to the monitor 710 and the viewing angle of the user toward the monitor 710 to thereby form and output first sensing signals corresponding thereto. The sensing unit 130 may further include second sensors $TS_1$ to $TS_4$ configured to detect a current posture (i.e., position) of the monitor 710 against the predetermined reference position of the monitor to thereby form and output second sensing signals corresponding thereto.

In the embodiment, any device may be employed as the first sensors $FS_1$ to $FS_4$ as long as the device can detect the position of the user, the distance between the user and the monitor 710, the height of the user with respect to the monitor and the viewing angle of the user toward the monitor 710, and form and output the sensing signals corresponding thereto. For example, the first sensors $FS_1$ to $FS_4$ may include at least one of a camera, a webcam and the like. The first sensors $FS_1$ to $FS_4$ may be provided inside or outside the monitor 710. Further, any device may be employed as the second sensors $TS_1$ to $TS_4$ as long as the device can detect the current attitude (i.e., position) of the monitor 710 against the predetermined reference position of the monitor, and form and output the sensing signals corresponding thereto. For example, the second sensors $TS_1$ to $TS_4$ include at least one of a gyro sensor, a tilt sensor and the like. The second sensors $TS_1$ to $TS_4$ may be provided inside or outside the monitor 710.

While the sensing unit 630 may include four first sensors $FS_1$ to $FS_4$ and four second sensors $TS_1$ to $TS_4$ in the above-described example, one of ordinary skill in the art will fully understand that the numbers as well as the positions of the first and second sensors can be varied as necessary, and not be limited to those described in this example.

Figure 9:
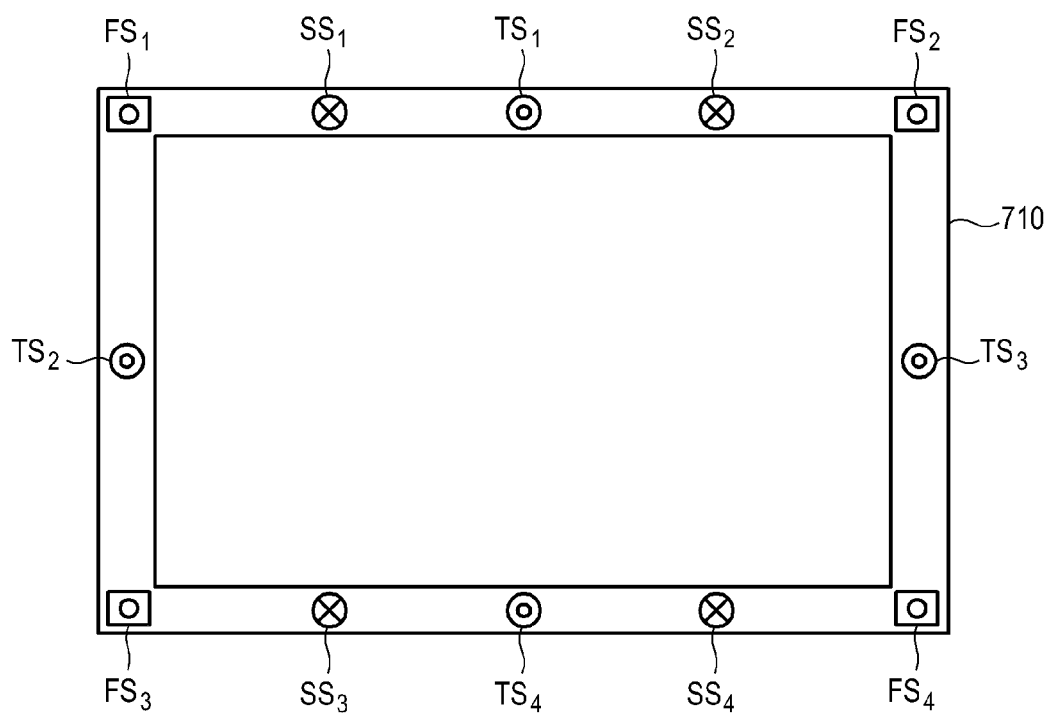
FIG. 9 is a schematic diagram showing another example of a sensing unit according to the second embodiment.

In another example, as shown in FIG. 9, the sensing unit 630, which is installed on one side (e.g., frame) of the monitor 710, may include first sensors $FS_1$ to $FS_4$ configured to detect the position of the user, the height of the user with respect to the monitor 710 and the viewing angle of the user toward the monitor 710 to thereby form and output first sensing signals corresponding thereto. The sensing unit 630 may further include second sensors $TS_1$ to $TS_4$ configured to detect the current attitude (i.e., position) of the monitor 710 against the predetermined reference position of the monitor to thereby form and output second signals corresponding thereto. The sensing unit 630 may further include third sensors $SS_1$ to $SS_4$ configured to detect the distance between the user and the monitor 710 to thereby form and output third sensing signals corresponding thereto. Any device may be employed as the third sensors $SS_1$ to $SS_4$ as long as the device can detect the distance between the user and the monitor 710, and form and output the sensing signals corresponding thereto. For example, the third sensors $SS_1$ to $SS_4$ may include a distance detecting sensor. The third sensors $SS_1$ to $SS_4$ may be provided inside or outside the monitor 710.

While the sensing unit 630 may include four first sensors $FS_1$ to $FS_4$, four second sensors $TS_1$ to $TS_4$ and four third sensors $SS_1$ to $SS_4$ in the above-described example, one of ordinary skill in the art will fully understand that the numbers as well as the positions of the first to third sensors can be varied as necessary, and not be limited to those described in this example.

The storage unit 640 may store optimal posture information for providing optimal ultrasound image for the posture of the user. In the present embodiment, the optimal posture information may include information on the optimal distance between the user and the monitor 710, the optimal height of the user with respect to the monitor 710 and the optimal viewing angle of the user toward the monitor 710.

The processing unit 650 may be coupled to the ultrasound data acquisition unit 610, the display unit 620, the sensing unit 630 and the storage unit 640. The processing unit 650 may include at least one of a central processing unit (CPU), a microprocessor unit, a graphic processing unit (GPU) and the like.

Figure 10:
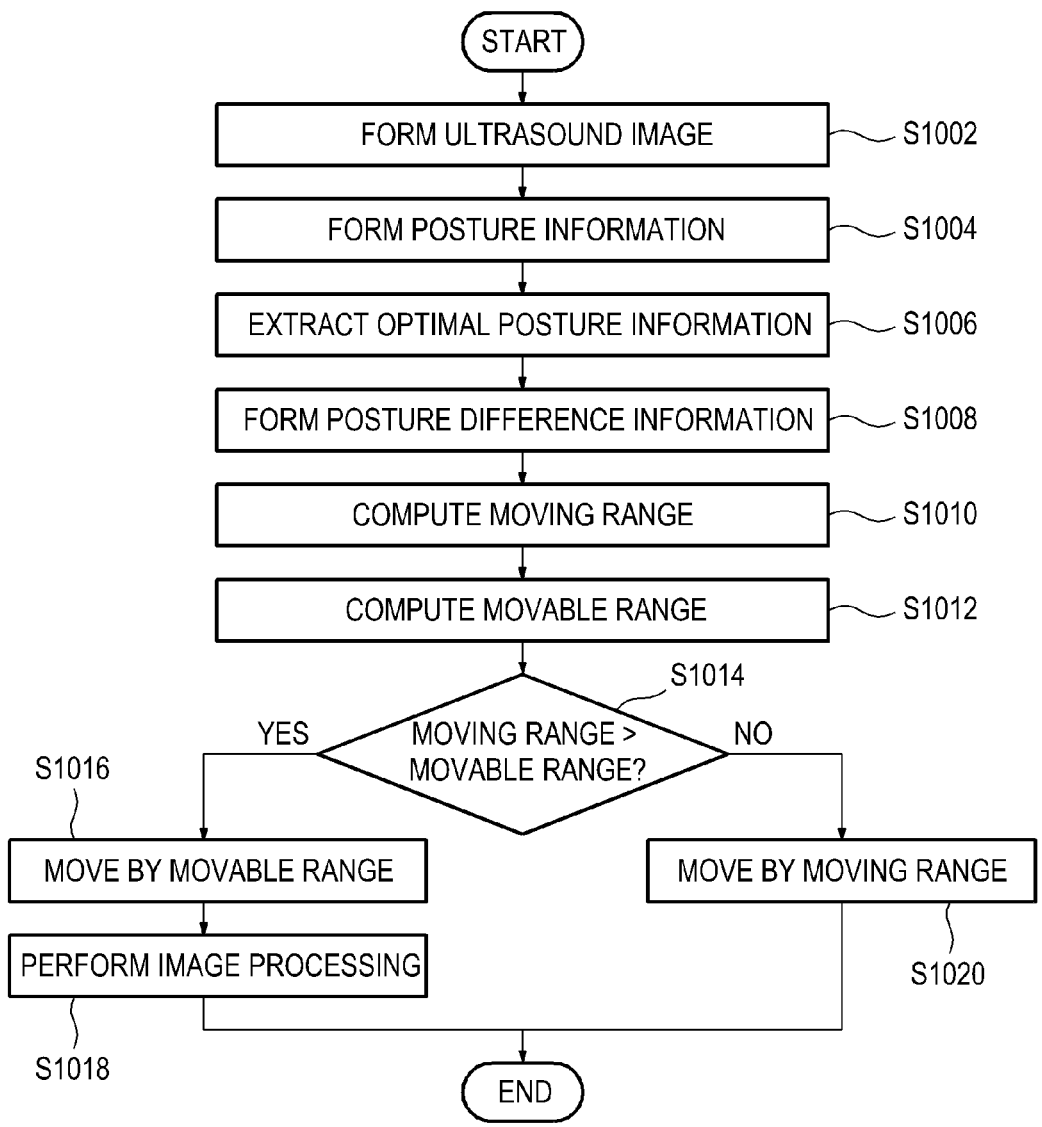
FIG. 10 is a flow chart showing a process of forming an optimal ultrasound image for posture of a user in accordance with the second embodiment.

FIG. 10 is a flow chart showing a process of forming the optimal ultrasound image for the user's posture in accordance with the second embodiment. Referring to FIG. 10, the processing unit 650 may produce the ultrasound image by using the ultrasound data provided from the ultrasound data acquisition unit 610 at S1002. The ultrasound image may be displayed on the monitor 710 of the display unit 620. The ultrasound image may be produced through scan conversion or rendering processing.

The processing unit 650 may form posture information based on the sensing signals provided from the sensing unit 630 at S1004. In the present embodiment, the posture information may include first posture information indicating the posture of the user with respect to the monitor 710 and second posture information indicating the position (i.e., attitude) of the monitor 710. The first posture information may include the distance between the user and the monitor 710, the height of the user with respect to the monitor 710 and the viewing angle of the user toward the monitor 710. However, the posture information may not be limited thereto.

In one example, the processing unit 650 may be provided with the first sensing signals from the first sensors $FS_1$ to $FS_4$ and detect the user's face (more preferably, the user's eyes) by using the provided first sensing signals. The user's face may be detected through vision recognition (i.e., image recognition) and the like. By using the detected user's face as a reference point, the processing unit 650 may calculate the distance between the monitor 710 and the user, the height of the user with respect to the monitor 710 (i.e., height of the user's eyes with respect to the monitor 710) and the viewing angle of the user toward the monitor 710. The distance, height and viewing angle can be calculated by using a variety of well-known methods so that the detailed description thereof will be omitted in the present embodiment. In this way, the processing unit 650 may form the first posture information including the calculated distance, height and viewing angle. Further, the processing unit 650, provided with the second sensing signals from the second sensors $TS_1$ to $TS_4$, may form the second posture information indicating the current attitude (e.g., tilt, rotation, etc.) of the monitor 710 by using the second sensing signals.

In another example, provided with the first sensing signals from the first sensors $FS_1$ to $FS_4$, the processing unit 650 may be configured to detect the user's face (more preferably, the user's eyes) by using the first sensing signals. The processing unit 650 may be configured to calculate the height of the user with respect to the monitor 710 (i.e., height of the user's eyes with respect to the monitor 710) and the viewing angle of the user toward the monitor 710 by utilizing the detected user's face as a reference point. Further, the processing unit 650, provided with the third sensing signals from the third sensors $SS_1$ to $SS_4$, may be configured to calculate the distance between the monitor 710 by using the third sensing signals. In this way, the processing unit 650 may be configured to form the first posture information including the calculated distance, height and viewing angle. Furthermore, the processing unit 650, provided with the second sensing signals from the second sensors $TS_1$ to $TS_4$, may form the second posture information indicating the current attitude (e.g., tilt, rotation, etc.) of the monitor 710 by using the second sensing signals.

The processing unit 650 may be configured to extract the optimal posture information from the storage unit 640 at S1006 and compare the extracted optimal posture information with the posture information to thereby acquire posture difference information at S1008. The posture difference information may include respective differential values of the distance, height and viewing angle. However, the posture information may not be limited thereto.

The processing unit 650 may be configured to compute a moving range of the monitor 710 based on the posture difference information at S1010. In this embodiment, the moving range is the range within which the monitor 710 may be moved to face the user's full face. The moving range may be computed by using various well-known methods. Thus, it will not be described in detail in the present embodiment.

Based on the posture information (i.e., the second posture information), the processing unit 650 may compute a movable range, which is the maximum range within which the monitor 710 can be moved in a three-dimensional direction (e.g., back/forth, right/left or the like) to face the user's full face at S1012.

The processing unit 650 may be configured to compare the computed moving range with the computed movable range at S1014. If it is determined that the moving range exceeds the movable range, then the processing unit 650 may move the monitor 710 as widely as the movable range by driving the driving section 720 at S1016. The processing unit 650 may perform image processing upon the ultrasound image to obtain the optimal image for the posture of the user at S1018. For example, the processing unit 650 may be configured to calculate the differential value between the moving range and the movable range and perform a process, which is similar to the step S510 in the first embodiment, in proportion to the calculated differential value.

Further, if it is determined that the moving range falls within the movable range, then the processing unit 650 may move the monitor 710 as widely as the moving range by driving the driving section 720 at S1020.

While the invention has been shown and described with reference to exemplary embodiments thereof, it will be understood by those skilled in the art that various changes in form and details may be made therein without departing from the spirit and scope of the invention as defined by the appended claims.

What is claimed is:

1. An ultrasound system, comprising:
    an ultrasound data acquisition unit including an ultrasound probe and being configured to transmit ultrasound signals to a target object and receive ultrasound echo signals reflected from the target object to thereby acquire initial ultrasound data;
    a display unit including a monitor and being configured to display an ultrasound image;
    a driving unit configured to move the monitor in a three-dimensional direction within a movable range;
    sensors installed on one side of the monitor and being configured to detect at least one of a position of a user, a distance between the user and the monitor, a height of the user with respect to the monitor, and a viewing angle of the user toward the monitor, to thereby form and output sensing signals corresponding thereto; and
    a processor coupled to the ultrasound data acquisition unit and the sensors, the processor being configured to control the display unit to display an ultrasound image optimized for a position of the user based on the sensing signals and the movable range,
    wherein the processor is further configured to:
        compute a moving range, which is a range within which the monitor is moved to face the user's full face, based on the sensing signals and optimal posture information,
        compare the moving range with the movable range and, if it is determined that the moving range exceeds the movable range, move the monitor as widely as the movable range by driving the driving unit,
        perform optimal image processing upon the ultrasound image based on a first differential value between the moving range and the movable range after moving the monitor as widely as the movable range by driving the driving unit, and to magnify/downscale the ultrasound image vertically or horizontally, or tilt/extend the ultrasound image toward the user, in proportion to a second differential value between the viewing angle and an optimal viewing angle, and
        compare the moving range with the movable range and, if it is determined that the moving range falls within the movable range, move the monitor as widely as the moving range by driving the driving unit.

2. The ultrasound system of claim 1, wherein the processor is further configured to control the display unit to display the ultrasound image by using the ultrasound data, the ultrasound image being formed by performing at least one process of magnify, downscale, tilt, extend, and rotate to an initial ultrasound image.

3. The ultrasound system of claim 1, wherein the sensors include:
    first sensors configured to detect the position of the user, the height of the user with respect to the monitor, and the viewing angle of the user toward the monitor, to thereby form and output first sensing signals corresponding thereto; and
    second sensors configured to detect the distance between the user and the monitor to thereby form and output second sensing signals corresponding thereto.

4. The ultrasound system of claim 1, further comprising a storage configured to store the optimal posture information including at least one of an optimal distance between the user and the monitor, an optimal height of the user with respect to the monitor, and the optimal viewing angle of the user toward the monitor.

5. The ultrasound system of claim 4, wherein the processor is further configured to form the ultrasound image by using the ultrasound data and to perform the optimal image processing for the posture of the user upon the ultrasound image based on the sensing signals and the optimal posture information.

6. The ultrasound system of claim 5, wherein the processor is further configured to:
    form posture information indicative of the position of the user with respect to the monitor based on the sensing signals,
    compare the optimal posture information with the posture information to form posture difference information, and
    perform the optimal image processing upon the ultrasound image based on the posture difference information and the posture information.

7. The ultrasound system of claim 6, wherein the posture information includes the distance between the monitor and the user, the height of the user with respect to the monitor and the viewing angle of the user toward the monitor.

8. The ultrasound system of claim 6, wherein the processor is further configured to:
    detect the user's face based on the sensing signals, and
    calculate the distance between the monitor and the user, the height of the user with respect to the monitor, and the viewing angle of the user toward the monitor, by using the detected user's face as a reference point.

* * * * *